(12) United States Patent
Takayasu et al.

(10) Patent No.: US 6,211,425 B1
(45) Date of Patent: Apr. 3, 2001

(54) PATCH

(75) Inventors: Toshiyuki Takayasu; Ikuhiro Kakubari; Norihiro Shinkai; Junji Kawakami; Noriko Nakajima; Akemi Uruno, all of Saitama-ken (JP)

(73) Assignee: Saitama Daiichi Seiyaku Kabushiki Kaisha, Kasukabe (JP)

( * ) Notice: Subject to any disclaimer, the term of this patent is extended or adjusted under 35 U.S.C. 154(b) by 0 days.

(21) Appl. No.: 09/254,367

(22) PCT Filed: Sep. 26, 1997

(86) PCT No.: PCT/JP97/03431

§ 371 Date: Mar. 4, 1999

§ 102(e) Date: Mar. 4, 1999

(87) PCT Pub. No.: WO98/14184

PCT Pub. Date: Apr. 9, 1998

(30) Foreign Application Priority Data

Oct. 4, 1996 (JP) .................................................. 8-283125

(51) Int. Cl.[7] .................................................. A61F 13/00
(52) U.S. Cl. .............................................. 602/41; 428/345
(58) Field of Search ................................ 602/41; 428/345, 428/355

(56) References Cited

U.S. PATENT DOCUMENTS 4,714,655 * 12/1987 Bordoloi et al. .

FOREIGN PATENT DOCUMENTS

| 59-9542 | 3/1984 | (JP) . |
|---|---|---|
| 60-174716 | 9/1985 | (JP) . |
| 63-22015 | 1/1988 | (JP) . |
| 1-311017 | 12/1989 | (JP) . |
| 2-78615 | 3/1990 | (JP) . |

* cited by examiner

*Primary Examiner*—Michael A. Brown
*Assistant Examiner*—Lalita M. Hamilton
(74) *Attorney, Agent, or Firm*—Frishauf, Holtz, Goodman, Langer & Chick, P.C.

(57) ABSTRACT

A transdermal patch containing a drug comprising formoterol and/or a salt, a solvent for the drug, a pressure-sensitive adhesive comprising an ethylene/vinyl acetate copolymer resin and at least one of a filler and a plasticizer. The patch is substantially water-free. The patch serves to promote percutaneous absorption of the formoterol and/or a salt thereof and allow the efficacy of the drug to stably persist for a long period of time. The patch is thus effective for diseases such as asthma, which can be cured or prevented by exciting β-receptors.

36 Claims, 1 Drawing Sheet

PATCH

TECHNICAL FIELD

The present invention relates to a patch which permits the sustained absorption of formoterol and is excellent in the long-term stability of formoterol and which is efficacious against asthma and other diseases to be treated or prevented through the excitation of β-receptors.

BACKGROUND ART

Formoterol exhibits pharmacological activities such as relaxation of bronchial smooth muscle through its selective actions on β-receptors in the sympathetic nervous system (see Japanese Patent Publication No. 9542/1984), and thus has been widely used in the treatment of chronic obstructive respiratory diseases, particularly bronchial asthma, with the purpose of ameliorating the dyspnea of patients with respiratory stenosis. Up to this time, formoterol has been orally administered in the form of tablets and dry syrups. In general, however, the oral administration of a remedy for a disease to be treated through the excitation of β-receptors often failed in suppressing or preventing attacks due to bronchial asthma or the like at night.

With respect to an integral transdermal system comprising an impermeable backing, a adhesive layer and a release liner, there has recently been disclosed a technique of forming the pressure-sensitive adhesive layer out of a mixture comprising a drug, a pressure-sensitive adhesive and a fluidity enhancer consisting of eucalyptol having a purity of 70% to thereby enhance the release of the drug from the system (see Japanese Patent Laid-Open No. 311017/1989).

Further, a multilayer patch has been disclosed, which comprises a cover sheet impermeable to the components of the reservoir layer which will now be described, a reservoir layer which is made from a mixture of an adhesive polymer with an optionally crosslinked block copolymer of styrene, an alkadiene and, if necessary, an alkene capable of being fed with an active substance, may be provided with an additional adhesive film at need, and contains an active substance capable of permeating the skin, a skin-permeation accelerator and, if necessary, a medical assistant, and a release film (see Japanese Patent Laid-Open No. 78615/1990).

However, the incorporation of formoterol into the pressure-sensitive adhesive layer of the above integral transdermal system or the reservoir layer of the above multilayer patch was disadvantageous in that the stability of formosterol was often problematic and that the high affinity of formoterol for the pressure-sensitive adhesive was causative of lowering the release of formoterol into the skin or hindering the extraction thereof in quantitative analysis.

SUMMARY OF INVENTION

The present the invention has been made under these circumferences, and aims at providing a preparation in which the feature of formoterol of acting on the $β_2$ receptor (a subtype of βreceptor) is utilized and which permits the smooth release of formoterol after administration without decay, can exert its pharmacological effects persistently for a prolonged time and is excellent in the long-term stability of formoterol.

The inventors of the present invention have made intensive studies in view of the above circumstances, and have found that formoterol and/or salts thereof, which are useful as drugs, exhibit extremely poor percutaneous absorption when they are not in a dissolved state, that the formoterol and/or salts thereof contained in preparations having high water contents are hydrolyzed fail in attaining excellent long-term stability, that when some kind of pressure-sensitive adhesive is used, formoterol and/or salts thereof are converted into such a state that cannot be extracted in quantitative analysis, or enveloped in the pressure-sensitive adhesive to result in such a state that cannot be extracted physically, and that when a percutaneously absorbable formoterol preparation excellent in the long-term stability of formoterol and the release thereof is applied to the skin, it can stimulate β-receptors over a long time and therefore serves to relax the bronchial smooth muscle in the treatment of asthma or the like. The present invention has been accomplished on the basis of these findings.

Namely, the present invention relates to a patch characterized by comprising formoterol or a salt thereof as the drug, a solvent for the drug, a pressure-sensitive adhesive, and a filler and/or a plasticizer, particularly a patch characterized by comprising formoterol or a salt thereof as the drug, a solvent for the drug, a pressure-sensitive adhesive, and a filler and/or a plasticizer, and being substantially free from water.

The patch of the present invention and the preparation thereof will now be described in detail.

The patch of the present invention is provided in a state wherein both a pressure-sensitive adhesive and a solvent for the drug are present in the preparation, preferably in a state wherein both a pressure-sensitive adhesive and a solvent for the drug are present in the preparation and the preparation is substantially free from water. As described above, formoterol is easily hydrolyzable, so that the long-term stability thereof in a patch is excellent as far as the patch is free from water. The drug to be used in the present invention may be not only formoterol itself but also a salt thereof. Such a formoterol salt includes salts of formoterol with inorganic acids such as hydrochloric acid and hydrobromic acid; and organic acids such as acetic acid, maleic acid and fumaric acid. Among these salts, formoterol fumarate is stably present as a hydrate, and some other formoterol salts can also take the form of hydrates. Such hydrates may be also used as the drug.

The solvent to be used in the present invention is not particularly limited, but may be any one as far as formoterol or salts thereof can be well dissolved therein. However, it is preferable to use a solvent in which the drug can be dissolved even when the solvent is used in a smaller amount. Examples of such a solvent include pyrrolidone (particularly 2-pyrrolidone); pyrrolidone derivatives such as N-methyl-2-pyrrolidone, 5-methyl-2-pyrrolidone, 1,5-dimethyl-2-pyrrolidone, 1-ethyl-2-pyrrolidone and 2-pyrrolidone-5-carboxylic acid; di- or tri-hydric alcohols such as glycerol, propylene glycol, 1,3-butylene glycol and polyethylene glycol; monohydric alcohols such as ethanol, isopropanol, oleyl alcohol and 2-octyldodecanol; and fatty acid esters such as diisopropyl adipate, oleyl oleate and diisopropyl sebacate, which may be used each alone or as a mixture of two or more of them.

The solvent to be used in the present invention includes not only solvents which are vaporized during the step of drying the patch but also those which remain in the preparation even after the completion of the drying step in a state containing the drug dissolved or dispersed therein.

The solvent often has an influence on the tackiness of the patch, the irritations thereof to the skin, the stability of the drug and so on in accordance with the kind and amount thereof, so that the compounding of the preparation must be conducted in consideration of the tackiness of the patch and the release and stability of the drug and so on. In particular, it is suitable to use N-methyl-2-pyrrolidone which has a high boiling point and high polarity. Although the amount of the solvent to be used varies depending on the solubility of the drug in the solvent and the kinds of other additives and cannot be therefore prescribed indiscriminately, it is suitable that the amount ranges from 0.1 to 20% by weight based on the whole composition. When N-methyl-2-pyrrolidone suitably usable in the present invention is used, the amount is preferably 0.01 to 10.0% by weight, still preferably 0.1 to 2.0% by weight based on the whole composition.

The pressure-sensitive adhesive to be used in the present invention may be one exhibiting such pressure-sensitive adhesive properties as to enable the patch to be held on the skin in a state adhering thereto at ordinary temperatures for a long time. Such a pressure-sensitive adhesive includes acrylic pressure-sensitive adhesives, silicon pressure-sensitive adhesives, ethylene/vinyl acetate copolymer resins (i.e., EVA pressure-sensitive adhesives) and so on. In particular, it is preferable to use one which permits the good release of formoterol or a salt thereof contained as the drug. The patch containing such a pressure-sensitive adhesive permits the speedy release of formoterol, and can be held on the skin stably for a prolonged time without fail.

Acrylic pressure-sensitive adhesives exhibit such pressure-sensitive adhesive properties as to enable the patch to be held on the skin in a state adhering thereto at ordinary temperatures for a long time. Accordingly, patches containing them can be held on the skin stably for a long time without fail. Although the composition of the acrylic pressure-sensitive adhesive to be used in the present invention is not particularly limited, it is suitable to use one or more members selected from among homopolymers and copolymers of (meth)acrylic esters of $C_1$–$C_{18}$ aliphatic alcohols and copolymers of these (meth)acrylic esters and other functional monomers.

Examples of the (meth)acrylic esters include methyl acrylate, ethyl acrylate, butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, methyl methacrylate, ethyl methacrylate, butyl methacrylate, isobutyl methacrylate, 2-ethylhexyl methacrylate, isooctyl methacrylate, decyl methacrylate, isodecyl methacrylate, lauryl methacrylate and stearyl methacrylate. Further, the silicone pressure-sensitive adhesive to be used in the present invention includes silicone rubbers such as polydimethylsiloxane, and ethylene/vinyl acetate copolymer resins (i.e., EVA pressure-sensitive adhesives) may be also used in the present invention.

Although the filler or plasticizer to be used in the present invention is not particularly limited, it is preferable to use one which exhibits high affinity for the pressure-sensitive adhesive and the solvent or absorption accelerator for the drug, can be retained in the patch stably without separation, inhibits the solvent and the absorption accelerator from causing phase separation, and permits excellent release of the drug. Examples of such a filler include polymers of vinylpyrrolidone and derivatives thereof such as polyvinylpyrrolidone; acrylic acid polymers such as linear polyacrylic acid and self-crosslinking polyacrylic acid; and cellulose derivatives such as ethylcellulose, methylcellulose and hydroxypropyl-cellulose. When an acrylic pressure-sensitive adhesive is used as the pressure-sensitive adhesive, the use of polyvinylpyrrolidone remarkably enhances the release of formoterol, being particularly desirable. The amount of polyvinylpyrrolidone to be used is preferably 0.01 to 10.0% by weight, still preferably 0.8 to 3.0% by weight based on the whole composition.

On the other hand, the plasticizer to be used in the present invention includes dioctyl adipate, glycerol, sesame oil, D-sorbitol, propylene glycol, polysorbate 80, polyethylene glycol, 1-menthol, cineol, oleic acid, oleyl alcohol, isopropyl adipate, octyldodecanol, diethyl sebacate, benzyl alcohol, isopropyl myristate, crotamiton, lauryl alcohol, 2-octyldodecanol, ethyl 2-ethylhexanoate, calcium thioglycolate, caprylic acid esters, decyl oleate, squalane and d-limonene, some of which have both properties of a filler and those of a plasticizer.

In particular, it is still preferable to use a filler and/or plasticizer having a percutaneous absorption accelerating effect. Examples of such a filler or plasticizer include 1-menthol, cineol, oleic acid, oleyl alcohol, diisopropyl adipate, octyldodecanol, diethyl sebacate, isopropyl myristate, crotamiton, lauryl alcohol, 2-octyldodecanol, decyl oleate and d-limonene.

These plasticizers and/or fillers having a percutaneous absorption accelerating effect may be used each alone or as a mixture of two or more of them. When 1-menthol or isopropyl myristate is used, the permeation through the skin of formoterol and/or a salt thereof to be used as the drug can be enhanced synergistically to thereby attain the percutaneous absorption of the drug at such a rate as to keep the effective blood concentration over a long time. The amount of the plasticizer and/or filler to be used may range from 0.01 to 95% by weight based on the whole composition. When 1-menthol is used, the amount is preferably 0.1 to 20.0% by weight, still preferably 1.0 to 10.0% by weight, while when isopropyl myristate is used, the amount is preferably 0.1 to 50.0% by weight, still preferably 10 to 35% by weight. A more excellent percutaneous absorption accelerating effect can be attained, when 1-menthol or isopropyl myristate is added to a system prepared by dissolving formoterol and/or a salt thereof in N-methyl-2-pyrolidone.

In the present invention, a drug which does not impair the effect of formoterol even in a state combined with formoterol or one which enhances the effect of formoterol additively or synergistically in a state combined therewith may be optionally used in addition to formoterol and/or a salt thereof. Examples of such a drug include xanthine derivatives such as theophylline and aminophylline; chlolilytic drugs such as ipratropium bromide and flutropium bromide; steroids such as beclomethasone; and antiallergic agents such as ketotifen, sodium cromoglicate, tranilast, and oxatomide. Further, other examples thereof include antitusives, expectorants, sedatives, antibiotics, and other drugs which do not impair the effect of formoterol or can enhance the effect thereof additively or synergistically.

In the present invention, various additives which have been used for patches at need or can be used therefor may be suitably used, and examples of such additives include surfactants such as sorbitan fatty acid esters, glycerol fatty acid esters, polyoxyethylene hydrogenated castor oil, polyoxyethylene stearyl ether, polyoxyethylene lauryl ether and sodium lauryl sulfate; pH regulators such as citric acid, tartaric acid, malic acid, phosphoric acid, lactic acid, maleic acid, diethanolamine, triethanolamine and diisopropanolamine; antioxidants such as sodium hydrogensulfite, dibutylhydroxytoluene, butylhydroxyanisole, sodium erythorbate, sodium edetate, ascorbic acid and propyl gallate; softeners such as paraffin, lanolin, rape seed oil, olive oil, almond oil, polyisoprene, propylene glycol, squalene, squalane and medium-chain fatty acid triglycerides; astringent agents such as aluminum chloride, magnesium metasilicate aluminate, aluminum sulfate, aluminum potassium sulfate and aluminum hydroxide; antiseptics such as butyl paraben and methyl paraben; stabilizers such as dextran, cacao butter and light anhydrous silicic acid; coloring matters, and flavors.

The patch of the present invention can be prepared by conventional processes employed in this field, for example, solvent processes, hot-melt processes or emulsion processes. In particular, a substantially water-free patch is preferably prepared by conducting the drying step at such a temperature as not to decompose formoterol to thereby evaporate water.

The patch of the present invention is generally provided in a state preliminarily applied or spread on a suitable base material. Although the base material to be used in the present invention is not particularly limited, it is preferably one soft enough not to give a sense of remarkable incongruity when the resulting patch is applied to the skin. Such a base material includes single-layer films, for example, plastic films of polyethylene, polypropylene, polyester, polyvinyl acetate, ethylene/vinyl acetate copolymers, polyvinyl chloride and polyurethane; metal foils such as aluminum foil and tin foil; nonwoven fabrics; cloth and papers; and laminated films comprising two or more of them. Further, it is preferable that the application face of the patch of the present invention be covered with a release liner such as paper or plastic film treated with a release agent until the point of time just before the application thereof to the skin.

According to a preferable application method, the patch of the present invention is rid of the release liner about 3 hours before the development of symptoms, and then the resulting patch is stuck on the skin with the application face toward the skin.

BEST MODE FOR CARRYING OUT THE INVENTION

Figure 1:
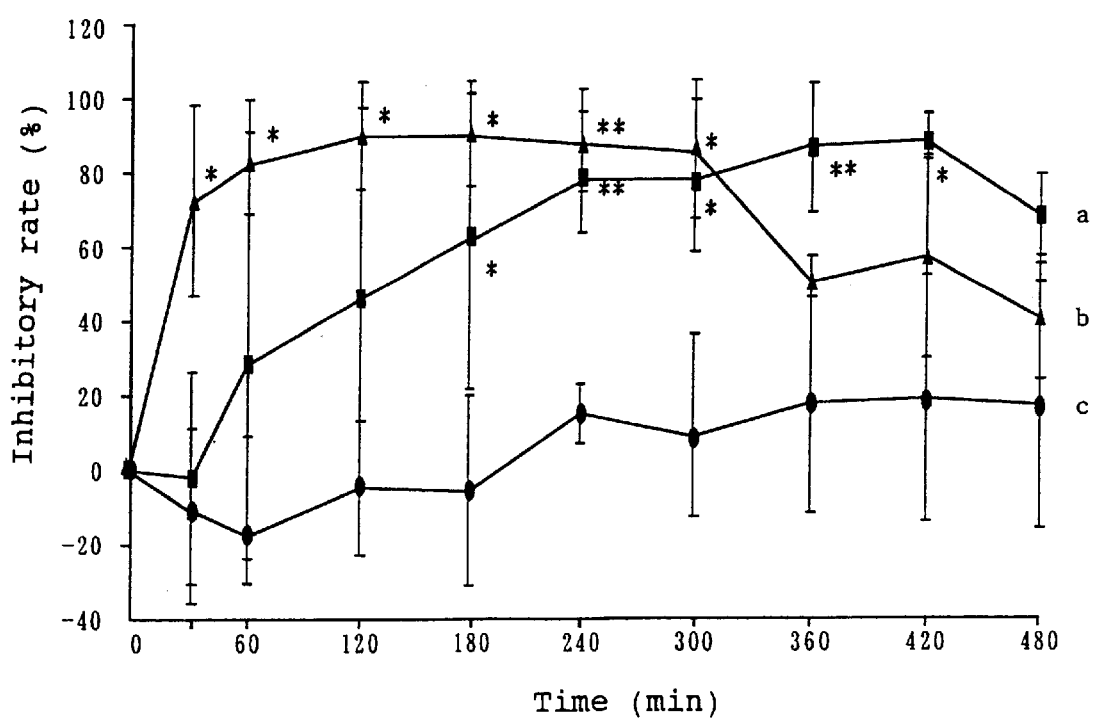
FIG. 1 is a graph showing changes in the inhibitory rate of histamine-induced airway resistance increasing reaction with the lapse of time.

The present invention will now be described in detail by referring to Examples, though the present invention is not limited by them.

EXAMPLE 1

Ethanol (4.0 g) and 1-menthol (4.0 g) were dissolved in a solution of 0.248 g of formoterol fumarate in 2.0 g of N-methyl-2-pyrrolidone. The obtained solution was added to 27.24 g of an acrylic pressure-sensitive adhesive [Nikasol TS-620 (trade name), a product of Nippon Carbide Industries Co., Inc.], followed by mixing. The pressure-sensitive adhesive mixture thus obtained was applied on a polyester film in a thickness of 150 $\mu$m, and dried to evaporate volatile components and water. A patch was obtained, which was substantially free from water, contained a solvent and had a plaster thickness of 55 $\mu$m.

EXAMPLE 2

Isopropanol (1.041 g) and polyvinylpyrrolidone (0.4 g) were dissolved in a solution of 0.248 g of formoterol fumarate in a mixture of 1.333 g of N-methyl-2-pyrrolidone with 0.694 g of propylene glycol. Diethyltoluamide (2.343 g) was added to the obtained solution, followed by mixing. The solution thus obtained was gradually added to 27.24 g of an acrylic pressure-sensitive adhesive [Nikasol TS-620 (trade name), a product of Nippon Carbide Industries Co., Inc.], followed by mixing. The pressure-sensitive adhesive mixture thus obtained was applied on a polyester film in a thickness of 150 $\mu$m, and dried to evaporate water. A patch was obtained, which was substantially free from water, contained a solvent and had a plaster thickness of 55 $\mu$m.

EXAMPLE 3

Ethanol (4.0 g), water (9.112 g) and polyvinylpyrrolidone (0.4 g) were added to a solution of 0.248 g of formoterol fumarate in 1.0 g of N-methyl-2-pyrrolidone, followed by mixing. The obtained solution was gradually added to 27.24 g of an acrylic pressure-sensitive adhesive [Nikasol TS-620 (trade name), a product of Nippon Carbide Industries Co., Inc.], followed by mixing. The pressure-sensitive adhesive mixture thus obtained was applied on a polyester film in a thickness of 150 $\mu$m, and dried to evaporate volatile components and water. A patch was obtained, which was substantially free from water, contained a solvent and had a plaster thickness of 55 $\mu$m.

EXAMPLE 4

Ethanol (4.0 g), isopropyl myristate (4.0 g) and polyvinylpyrrolidone (0.4 g) were added to a solution of 0.248 g of formoterol fumarate in 2.0 g of N-methyl-2-pyrrolidone, followed by mixing. The solution thus obtained was added to 29.42 g of an acrylic pressure-sensitive adhesive [Nikasol TS-620 (trade name), a product of Nippon Carbide Industries Co., Inc.] The pressure-sensitive adhesive mixture thus obtained was applied on a polyester film in a thickness of 150 $\mu$m, and dried to evaporate volatile components and water. A patch was obtained, which was substantially free from water, contained a solvent and had a plaster thickness of 55 $\mu$m.

EXAMPLE 5

Ethanol (4.0 g), 1-menthol (4.0 g), water (4.112 g) and polyvinylpyrrolidone (0.4 g) were added to a solution of 0.248 g of formoterol fumarate in 2.0 g of N-methyl-2-pyrrolidone, followed by mixing. The solution thus obtained was added to 27.24 g of an acrylic pressure-sensitive adhesive [Nikasol TS-620 (trade name), a product of Nippon Carbide Industries Co., Inc.], followed by mixing. The pressure-sensitive adhesive mixture thus obtained was applied on a polyester film in a thickness of 150 $\mu$m, and dried to evaporate volatile components and water. A patch was obtained, which was substantially free from water, contained a solvent and had a plaster thickness of 55 $\mu$m.

EXAMPLE 6

Isopropanol (1.041 g) and polyvinylpyrrolidone (0.4 g) were dissolved in a solution of 0.248 g of formoterol fumarate in 1.333 g of octyldodecanol. Diethyl-toluamide (2.343 g) was added to the obtained solution, followed by mixing. The solution thus obtained was gradually added to 27.24 g of an acrylic pressure-sensitive adhesive [Nikasol TS-620 (trade name), a product of Nippon Carbide Industries Co., Inc.] and disolved. The pressure-sensitive adhesive mixture thus obtained was applied on a polyester film in a thickness of 150 $\mu$m, and dried to evaporate water. A patch was obtained, which was substantially free from water, contained a solvent and had a plaster thickness of 55 $\mu$m.

EXAMPLE 7

Ethanol (4.0 g), water (4.112 g) and isopropyl myristate (0.4 g) were dissolved in a solution of 0.248 g of formoterol in 2.0 g of octyldodecanol. The solution thus obtained was added to 27.24 g of an acrylic pressure-sensitive adhesive [Primal N-580 (trade name), a product of Nippon Carbide Industries Co., Inc.], followed by mixing. The pressure-sensitive adhesive mixture thus obtained was applied on a polyester film in a thickness of 150 µm, and dried to evaporate volatile components and water. A patch was obtained, which was substantially free from water, contained a solvent and had a plaster thickness of 55 µm.

EXAMPLE 8

Ethanol (4.0 g) and 1-menthol (4.0 g) were dissolved in a solution of 0.248 g of formoterol fumarate in 2.0 g of N-methyl-2-pyrrolidone. The obtained solution was added to 27.24 g of an ethylene/vinyl acetate copolymer resin [EVAFLEX (trade name), a product of Du Pont-Mitsui Chemicals Co., Ltd.], followed by mixing. The pressure-sensitive adhesive mixture thus obtained was applied on a polyester film in a thickness of 150 µm, and dried to evaporate volatile components and water. A patch was obtained, which was substantially free from water, contained a solvent and had a plaster thickness of 55

EXAMPLE 9

Ethanol (4.0 g) and 1-menthol (4.0 g) were dissolved in a solution of 0.248 g of formoterol fumarate in 2.0 g of propylene glycol. The obtained solution was added to 27.24 g of an ethylene/vinyl acetate copolymer resin [EVAFLEX (trade name), a product of Du Pont-Mitsui Chemicals Co., Ltd.], followed by mixing. The pressure-sensitive adhesive mixture thus obtained was applied on an aluminum film in a thickness of 150 µm, and dried to evaporate volatile components and water. A patch was obtained, which was substantially free from water, contained a solvent and had a plaster thickness of 55 µm.

COMPARATIVE EXAMPLE 1

Formoterol fumarate (0.062 g) was added to 6.608g of water, followed by mixing. The obtained solution was added to 33.33 g of an acrylic pressure-sensitive adhesive [Nikasol TS-620 (trade name), a product of Nippon Carbide Industries Co., Inc.], followed by mixing. The pressure-sensitive adhesive mixture thus obtained was applied on a polyester film in a thickness of 100 µm, and dried to evaporate volatile components. A patch was obtained, which was free from a solvent and had a plaster thickness of 55 µm.

COMPARATIVE EXAMPLE 2

Toluene (10.8 g) was added to a mixture of 1.0 g of a 6.2% solution of formoterol fumarate in methanol with 9.1 g of a silicone pressure-sensitive adhesive base [PSA 6574 (trade name), a product of Toshiba Silicone Co., Ltd.], followed by mixing. The pressure-sensitive adhesive mixture thus obtained was applied on a polyester film in a thickness of 200 µm, and dried to evaporate volatile components. A patch was obtained, which was free from a solvent and had a plaster thickness of 55 µm.

COMPARATIVE EXAMPLE 3

A 6.2% solution (1.0 g) of formoterol fumarate in methanol was added to a solution prepared by dissolving 2.0 g of a styrene/isoprene/styrene block copolymer [KRATON D-1107CP (trade name), a product of Shell Japan Ltd.], 2.9 g of an alicyclic saturated hydrocarbon resin [Arkon P-90 (trade name), a product of Arakawa Chemical Industries Ltd.)] and 0.1 g of dibutylhydroxytoluene in 14.0 g of toluene, followed by mixing. The pressure-sensitive adhesive mixture thus obtained was applied on a polyester film in a thickness of 200 µm, and dried to evaporate volatile components. A patch was obtained, which was free from a solvent and had a plaster thickness of 55 µm.

COMPARATIVE EXAMPLE 4

A 6.2% solution (1.0 g) of formoterol fumarate in methanol was added to a solution of 5.0 g of an ethylene/vinyl acetate copolymer resin [EVAFLEX 45X (trade name), a product of Du Pont-Mitsui Chemicals Co., Ltd.] in 14.0 g of toluene, followed by mixing. The pressure-sensitive adhesive mixture thus obtained was applied on a polyester film in a thickness of 200 µm, and dried to evaporate volatile components. A patch was obtained, which was free from a solvent and had a plaster thickness of 55 µm.

COMPARATIVE EXAMPLE 5

Formoterol fumarate (0.372 g) was added to 5.0 g of methanol, followed by the addition of 5.0 g of ethanol. 1-Menthol (10.0 g ) and purified water (1.168 g) were added to the solution prepared above, followed by the addition of 0.60 g of polyvinylpyrrolidone. The obtained solution was added to 40.86 g of an acrylic pressure-sensitive adhesive [Nikasol TS-620 (trade name), a product of Nippon Carbide Industries Co., Inc.], followed by mixing. The pressure-sensitive adhesive mixture thus obtained was applied on a polyester film in a thickness of 150 µm, and dried to such a level that the methanol and ethanol were completely removed with water left at a content of about 0.5% or above. Thus, a patch substantially containing water was obtained.

TEST EXAMPLE 1

Rat Cutaneous Permeation Test

To compare patches containing solvents with solvent-free one in the percutaneous absorbability of formoterol contained therein, an experiment was made on the permeation of formoterol through the living body skin according to a rat cutaneous permeation test. The patches of Examples 1, 2, 3, 4 and 8 and Comparative Example 4 were examined for quantity of the drug passed through the abdominal skin of a Wistar male rat having a weight of 170 to 200 g. This examination was conducted at 37° C. by using a Franz diffusion cell as the equipment and physiological saline as the receiver solution. A rat skin was put in the upper section the Franz diffusion cell, and a 1.1-cm diameter test piece punched out of each patch was fixed on the rat skin. After the lapse of 2, 4, 6, 8 and 24 hours from the fixing, samples of the receiver solution of 0.3 ml in volume were taken out, immediately followed by the supplement of the same amount of physiological saline. The samples were pretreated, and subjected to HPLC to determine the quantities of the drug passed through the rat skin. The results are given in Table 1 (in terms of average of three samples and in $\mu g/cm^2$).

TABLE 1

| Time (hr) | Ex. 1 | Ex. 2 | Ex. 3 | Ex. 4 | Ex. 8 | Comp. Ex. 4 |
|---|---|---|---|---|---|---|
| 2 | 0.55 | 0.39 | 0.98 | 1.20 | 0.13 | 0.04 |
| 4 | 1.31 | 0.93 | 2.24 | 3.01 | 0.66 | 0.04 |
| 6 | 1.99 | 1.69 | 3.13 | 4.34 | 1.65 | 0.05 |

TABLE 1-continued

| Time (hr) | Ex. 1 | Ex. 2 | Ex. 3 | Ex. 4 | Ex. 8 | Comp. Ex. 4 |
|---|---|---|---|---|---|---|
| 8 | 2.32 | 2.37 | 3.47 | 6.43 | 2.77 | 0.06 |
| 24 | 4.22 | 8.00 | 6.71 | 16.97 | 8.09 | 0.67 |

(Quantity of drug passed: $\mu g/cm^2$)

As understood from the above results, the patches of Examples 1 to 4 and 8 permit sustained permeation of formoterol through the skin as compared with the one of Comparative Example 4, thus being excellent in percutaneous absorption.

TEST EXAMPLE 2

The substantially water-free patch of Example 5 was quantitatively compared with the water-containing one of Comparative Example 5 in the long-term stability of formoterol contained therein by high-performance liquid chromatography. Table 2 shows the retentions of formoterol.

TABLE 2

| Storage conditions | Ex. 5 | Comp. Ex. 5 |
|---|---|---|
| 40° C./2 wk | 101.1 | 94.9 |
| 40° C./8 wk | 96.1 | 77.8 |

(% based on the initial amt.)

As understood from the above results, the substantially water-free patch of Example 5 exhibits more excellent long-term stability of formoterol than that of the water-containing patch of Comparative Example 5.

TEST EXAMPLE 3

Release Test

The patches of Example 1 and Comparative Examples 1 to 4 were examined for rate of release of formoterol therefrom with the lapse of time. This examination was conducted at 37° C. by using a Franz diffusion cell as the equipment and physiological saline as the receiver solution. A 1.0-cm diameter test piece punched out of each patch was fixed in the upper section of the Franz diffusion cell. At prescribed time intervals, samples of the receiver solution of 0.5 ml in volume were taken out, immediately followed by the supplement of the same amount of physiological saline. A methanol solution containing an internal standard was added to each sample and the resulting mixture was subjected to HPLC to determine the amount of formoterol released. The results are given in Table 3 (in terms of average of three samples).

TABLE 3

| Time (hr) | Ex. 1 | Comp. Ex. 1 | Comp. Ex. 2 | Comp. Ex. 3 | Comp. Ex. 4 |
|---|---|---|---|---|---|
| 0.5 | 61.8 | 10.0 | 0.8 | 17.3 | 15.6 |
| 1 | 71.0 | 10.9 | 1.0 | 30.9 | 22.0 |
| 1.5 | 74.8 | 11.9 | 1.6 | 36.7 | 24.1 |
| 2 | 77.6 | 12.7 | 1.3 | 40.5 | 25.4 |
| 3 | 80.3 | 13.3 | 1.2 | 44.6 | 26.2 |
| 4 | 81.0 | 14.1 | 0.7 | 46.9 | 26.8 |
| 6 | 81.5 | 15.2 | 0.7 | 49.8 | 27.3 |
| 8 | 81.5 | 16.3 | 0.7 | 50.5 | 27.1 |

(Amt. of formoterol released: %)

As understood from the above results, the rates of release of formoterol from the solvent-free patches of Comparative Examples 1 to 4 were remarkably lower than that thereof from the solvent-containing one of Example 1. The patch of Comparative Example 1 gradually released the drug, but the amount of the drug released was only about 15%. The patch of Comparative Example 2 little released the drug. The patches of Comparative Examples 3 and 4 released the drug till the lapse of about 2 hours, but no release of the drug therefrom was found after the lapse of 2 hours. The rates of release of the patches of Comparative Examples 3 and 4 were as low as about 50% and 27% (about one-forth), respectively. On the other hand, the solvent-containing patch of Example 1 reached the maximum amount of the drug released in a short time, and released about 90% of the drug, thus being excellent in the release of the drug.

TEST EXAMPLE 4

Guinea Pig Pharmacological Test

The patch of Example 5 was applied to a guinea pig to determine the percutaneous absorbability and persistency of formoterol. Histamine was intra-venously administered to a Hartley guinea pig (weight: 500 to 750 g) whose abdomen had preliminarily been depilated with a depilatory cream the day before the test in a dose of 3 $\mu g/kg$ at 30 minute intervals. After the airway resistance had increased to a constant level, the patch of Example 5 was applied to the depilated abdomen. 30 minutes and 60 minutes after the application, and then at hourly intervals, histamine was administered to the guinea pig to cause an airway constricting reaction. The inhibitory rates were calculated based on the airway resistance value observed before the administration of the drug. For comparison, inhibitory rates were calculated also in the case wherein formoterol was orally administered to a guinea pig and in the (untreated) case wherein no drug was administered thereto.

FIG. 1 shows changes in the rate of inhibition of histamine-induced airway resistance increasing reaction by formoterol with the lapse of time (in terms of average of three samples). In FIG. 1, curve a shows the results found in the case wherein the patch of Example 5 was applied, curve b shows those found in the case wherein formoterol was orally administered, and curve c shows those found in the untreated case.

As understood from the above results, the patch of the present invention exerts the effect persistently over a prolonged period of 6 hours or longer after the application, exhibits a satisfactory inhibitory activity and is extremely excellent in percutaneous absorbability and persistency, though the activity development time of the patch is longer than that of oral administration of formoterol.

INDUSTRIAL APPLICABILITY

As described above, the present invention provides a patch useful as antiasthmatic drug or the like which permits high release of formoterol and high permeation thereof through the skin, and has an effect of exciting β-receptors over a prolonged time to exert a curative effect through the relaxation of bronchial smooth muscle over a prolonged time persistently without fail.

What is claimed is:

1. A substantially water-free transdermal patch comprising:
   (a) a drug comprising at least one of formoterol and a salt of formoterol,
   (b) 0.1 to 20% by weight based on the weight of the transdermal patch of a solvent for the drug,
   (c) a pressure-sensitive adhesive comprising an ethylene/vinyl acetate copolymer resin, and (d) 0.01 to 95% by weight based on the weight of the transdermal patch of at least one of a filler and a plasticizer.

2. The transdermal patch according to claim 1, wherein the drug is a formoterol salt which is formoterol fumarate.

3. The transdermal patch according to claim 2, wherein the at least one of the filler and the plasticizer exhibits a percutaneous absorption accelerating effect.

4. The transdermal patch according to claim 3, wherein the at least one of the filler and the plasticizer exhibiting a percutaneous absorption accelerating effect is at least one compound selected from the group consisting of a terpene and a fatty acid ester.

5. The transdermal patch according to claim 4, wherein the at least one of the filler and the plasticizer is a terpene which is 1-menthol.

6. The transdermal patch according to claim 4, wherein the at least one of the filler and the plasticizer is a fatty acid ester which is isopropyl myristate.

7. The transdermal patch according to claim 1, wherein the solvent is at least one pyrrolidone compound.

8. The transdermal patch according to claim 2, wherein the solvent is at least one pyrrolidone compound.

9. The transdermal patch according to claim 8, wherein the pyrrolidone derivative is N-methyl-2-pyrrolidone.

10. The transdermal patch according to claim 9, wherein the at least one of the filler and the plasticizer exhibits a percutaneous absorption accelerating effect.

11. The transdermal patch according to claim 10, wherein the at least one of the filler and the plasticizer exhibiting a percutaneous absorption accelerating effect is at least one compound selected from the group consisting of a terpene and a fatty acid ester.

12. The transdermal patch according to claim 11, wherein the at least one of the filler and the plasticizer is a terpene which is 1-menthol.

13. The transdermal patch according to claim 11, wherein the at least one of the filler and the plasticizer is a fatty acid ester which is isopropyl myristate.

14. The transdermal patch according to claim 8, wherein the at least one of the filler and the plasticizer exhibits a percutaneous absorption accelerating effect.

15. The transdermal patch according to claim 14, wherein the at least one of the filler and the plasticizer exhibiting a percutaneous absorption accelerating effect is at least one compound selected from the group consisting of a terpene and a fatty acid ester.

16. The transdermal patch according to claim 15, wherein the at least one of the filler and the plasticizer is a terpene which is 1-menthol.

17. The transdermal patch according to claim 15, wherein the at least one of the filler and the plasticizer is a fatty acid ester which is isopropyl myristate.

18. The transdermal patch according to claim 7, wherein the pyrrolidone compound is N-methyl-2-pyrrolidone.

19. The transdermal patch according to claim 18, wherein the at least one of the filler and the plasticizer exhibits a percutaneous absorption accelerating effect.

20. The transdermal patch according to claim 19, wherein the at least one of the filler and the plasticizer exhibiting a percutaneous absorption accelerating effect is at least one compound selected from the group consisting of a terpene and a fatty acid ester.

21. The transdermal patch according to claim 20, wherein the at least one of the filler and the plasticizer is a terpene which is 1-menthol.

22. The transdermal patch according to claim 20, wherein the at least one of the filler and the plasticizer is a fatty acid ester which is isopropyl myristate.

23. The transdermal patch according to claim 7, wherein the at least one of the filler and the plasticizer exhibits a percutaneous absorption accelerating effect.

24. The transdermal patch according to claim 23, wherein the at least one of the filler and the plasticizer exhibiting a percutaneous absorption accelerating effect is at least one compound selected from the group consisting of a terpene and a fatty acid ester.

25. The transdermal patch according to claim 24, wherein the at least one of the filler and the plasticizer is a terpene which is 1-menthol.

26. The transdermal patch according to claim 24, wherein the at least one of the filler and the plasticizer is a fatty acid ester which is isopropyl myristate.

27. The transdermal patch according to claim 1, wherein the at least one of the filler and the plasticizer exhibits a percutaneous absorption accelerating effect.

28. The transdermal patch according to claim 27, wherein the at least one of the filler and the plasticizer exhibiting a percutaneous absorption accelerating effect is at least one compound selected from the group consisting of a terpene and a fatty acid ester.

29. The transdermal patch according to claim 28, wherein the at least one of the filler and the plasticizer is a terpene which is 1-menthol.

30. The transdermal patch according to claim 28, wherein the at least one of the filler and the plasticizer is a fatty acid ester which is isopropyl myristate.

31. The transdermal patch according to claim 1, wherein the pyrrolidone compound is selected from the group consisting of N-methyl-2-pyrrolidone, 5-methyl-2-pyrrolidone, 1,5-dimethyl-2-pyrrolidone, 1-ethyl-2-pyrrolidone, 2-pyrrolidone-5-carboxylic acid, glycerol, propylene glycol, 1,3-butylene glycol, polyethylene glycol, ethanol, isopropanol, oleyl alcohol, 2-octyldodecanol, diisopropyl adipate, oleyl oleate and diisopropyl sebacate.

32. The transdermal patch according to claim 31, wherein the solvent is N-methyl-2-pyrrolidone and is in an amount of 0.01 to 10.0% by weight based on the weight of the patch.

33. The transdermal patch according to claim 32, wherein the solvent is in an amount of 0.1 to 2.0% by weight based on the weight of the patch.

34. The transdermal patch according to claim 33, wherein the at least one of the filler and the plasticizer is at least one compound selected from the group consisting of a terpene and a fatty acid ester.

35. The transdermal patch according to claim 34, wherein the at least one of the filler and the plasticizer is a terpene which is 1-menthol.

36. The transdermal patch according to claim 34, wherein the at least one of the filler and the plasticizer is a fatty acid ester which is isopropyl myristate.

* * * * *